United States Patent
Macgowan et al.

(10) Patent No.: US 6,507,749 B1
(45) Date of Patent: Jan. 14, 2003

(54) METHOD AND APPARATUS FOR TRACKING THE MOTION OF FLUID AND DETERMINING A VELOCITY SPECTRUM THEREOF FROM MR DATA ACQUIRED IN A SINGLE CYCLE

(75) Inventors: Christopher K. Macgowan, Toronto (CA); Michael L. Wood, Toronto (CA)

(73) Assignee: Sunnybrook and Women's College, Toronto (CA)

(*) Notice: Subject to any disclaimer, the term of this patent is extended or adjusted under 35 U.S.C. 154(b) by 0 days.

(21) Appl. No.: 09/682,087

(22) Filed: Jul. 18, 2001

(51) Int. Cl.⁷ .................................................. A61B 5/05
(52) U.S. Cl. ........................ 600/419; 324/307; 324/309
(58) Field of Search .......................... 600/419; 324/307, 324/309

(56) References Cited

U.S. PATENT DOCUMENTS 5,054,489 A * 10/1991 Axel et al. ............... 128/653 A
5,133,357 A * 7/1992 Dumoulin et al. ....... 128/653.3
5,417,214 A * 5/1995 Roberts et al. .......... 128/653.3

OTHER PUBLICATIONS

Magnetic Resonance in Medicine 45:461–469 (2001) Fast measurments of the motion and velocity spectrum of blood using MR tagging.

* cited by examiner

Primary Examiner—Marvin M. Lateef
Assistant Examiner—Devaang Shah
(74) Attorney, Agent, or Firm—Ziolkowski Patent Solutions Group, LLC; Michael A. Della Penna; Carl B. Horton

(57) ABSTRACT

The present invention is directed to a method and system for tracking the motion of fluid traveling through a vessel and determining its velocity spectrum from magnetic resonance data collected within a single cycle. The present invention provides a process of independently acquiring and processing MR data from a single cardiac cycle. By combining a SPAMM excitation with a two-dimensional selective excitation, suitable tags of fluid flowing through the vessel may be created. The combination of the excitations produces a sinusoidal variation of transverse magnetization along a column of the fluid. A succession of gradient echoes are then collected to provide information about the flow of fluid in the excited vessel. Each gradient echo undergoes a transformation to obtain a 1-D projection of the excited fluid across the vessel. The magnitudes of the projections are then used to construct a velocity spectrum of the fluid.

28 Claims, 4 Drawing Sheets

METHOD AND APPARATUS FOR TRACKING THE MOTION OF FLUID AND DETERMINING A VELOCITY SPECTRUM THEREOF FROM MR DATA ACQUIRED IN A SINGLE CYCLE

BACKGROUND OF INVENTION

The present invention relates generally to measuring the velocity spectrum of fluid traveling through a vessel and, more particularly to, a method and apparatus for tracking the motion of fluid and determining a velocity spectrum thereof from MR data acquired in a single cycle.

Determining and subsequent analyzing of flow characteristics of fluid flowing through a vessel have a number of applications, but are particularly applicable to the assessment of cardiovascular conditions. Quantitative measurements of blood motion may be used to assess the severity of vascular stenoses, the volumetric blood flow to tissues, and the mechanical properties of vessel walls. Known techniques implement non-invasive Doppler ultrasound to acquire quantitative measurements of blood through a vessel. Doppler ultrasound, however, has limited applicability because it is unable to access all vessels in some patients.

Other known techniques implement magnetic resonance (MR) technology to obtain measurements of blood motion. Current MR techniques have a number of advantages over Doppler ultrasound and include the ability to view entire vessels anywhere in the body, regardless of vessel angle, depth, and acoustic window. Notwithstanding the capability to interrogate vessels anywhere in the body, these known MR systems acquire measurements of blood motion very slowly and often require that data be combined from multiple cardiac cycles to provide usable measurements. Specifically, traditional MR techniques must often combine data from several cycles to improve the temporal resolution of the MR measurements.

Requiring data acquisition from several cardiac cycles to provide usable MR measurements of blood motion exposes the measurement process to the risk of gross patient motion often associated with longer scans that can have detrimental effects on image reconstruction. Further, over time, a periodic motion will introduce complex distortions to the MR measurements.

Several techniques have been developed to rapidly measure physiological motion using MR imaging processes. One such technique includes cardiac tagging to measure the motion and mechanical properties of the heart. Other known techniques have implemented tagging to visualize fluid flow. These known tagging techniques however, fail to accommodate signals produced by static tissue or signals produced by a range of blood velocities. Failure to recognize the impact of this velocity spectrum ultimately affects the accuracy of any blood displacement measurements acquired using tagging. Moreover, known cardiac tagging techniques are not able to provide accurate measurements of blood motion within a single heartbeat and at a high temporal resolution.

It would therefore be desirable to design a method and apparatus for tracking the motion of blood and determining its velocity spectrum from MR data collected within a single cardiac cycle. It would be further desirable to design a system for calculating a velocity spectrum that can be used to assess and/or remove any signals produced by static tissue to generate more accurate blood displacement measurements.

SUMMARY OF INVENTION

The present invention is directed to a method and system for tracking the motion of fluid traveling through a vessel and determining its velocity spectrum from magnetic resonance data collected within a single cycle. The present invention provides a method of independently acquiring and processing MR data from a single cardiac cycle. By combining a Spatial Modulation of Magnetization (SPAMM) excitation with a two-dimensional selective excitation positioned within a vessel, suitable tags of fluid flowing through the vessel may be created. This combination produces a sinusoidal variation of transverse magnetization along a column of the fluid. A succession of gradient echoes are then collected after the excitation to provide information about the flow of fluid in the excited vessel. Each gradient echo undergoes a transformation, i.e., such as Fourier transformation, to obtain a 1-D projection of the excited fluid across the vessel. The magnitude of each 1-D projection is then used to construct a velocity spectrum of the fluid flowing through the vessel. All of which overcomes the aforementioned drawbacks.

Therefore, in accordance with an aspect of the present invention, a method of measuring velocity of fluid flow in a vessel comprises the steps of identifying a vessel for fluid flow analysis and applying a pulse sequence to the vessel to excite fluid in the vessel. Application of the pulse sequence to the vessel further produces a sinusoidal variation of transverse magnetization along a column of fluid in the identified vessel. The method further includes the steps of acquiring a set of gradient echoes from the excited fluid where each gradient echo represents a 1-D projection of the excited fluid across the vessel and tracking the evolution of at least a portion of the 1-D projections. The method also includes the step of developing a velocity spectrum from the evolution tracking.

In accordance with a further aspect of the present invention, a computer program is provided that when executed by the computer causes the computer to apply a SPAMM excitation and cylindrical excitation to fluid flowing through a vessel. The computer is also programmed to acquire a set of gradient echoes from excited portions of fluid flowing through the vessel and determine a projection from each gradient echo. The computer program further causes the computer to organize the projections into a number of subsets where each subset represents a single projection and to modulate the projection of each subset to remove phase variations from the projections. The computer program further causes the computer to determine the magnitude of each projection and develop an evolutionary map representative of projection magnitude over time.

In accordance with yet a further aspect of the present invention, an MR apparatus includes an MRI system having a plurality of coils positioned about the bore of a magnet to impress a polarizing magnetic field. The MRI system further includes an RF transceiver system and an RF switch controlled by a pulse module to transmit and receive RF signals to and from a multi-coil RF coil assembly to acquire MR images. The MR apparatus further includes a computer programmed to apply a tagging sequence to a vessel to excite blood flowing through the vessel and to produce a sinusoidal variation of transverse magnetization along a region of blood in the vessel. The computer is further programmed to acquire a series of gradient echoes from the excited blood in a single cardiac cycle and transform each gradient echo to produce a corresponding 1-D projection. The computer is also programmed to analyze the 1-D projections to determine an evolutionary pattern of blood velocity.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings.

DETAILED DESCRIPTION

Figure 1:
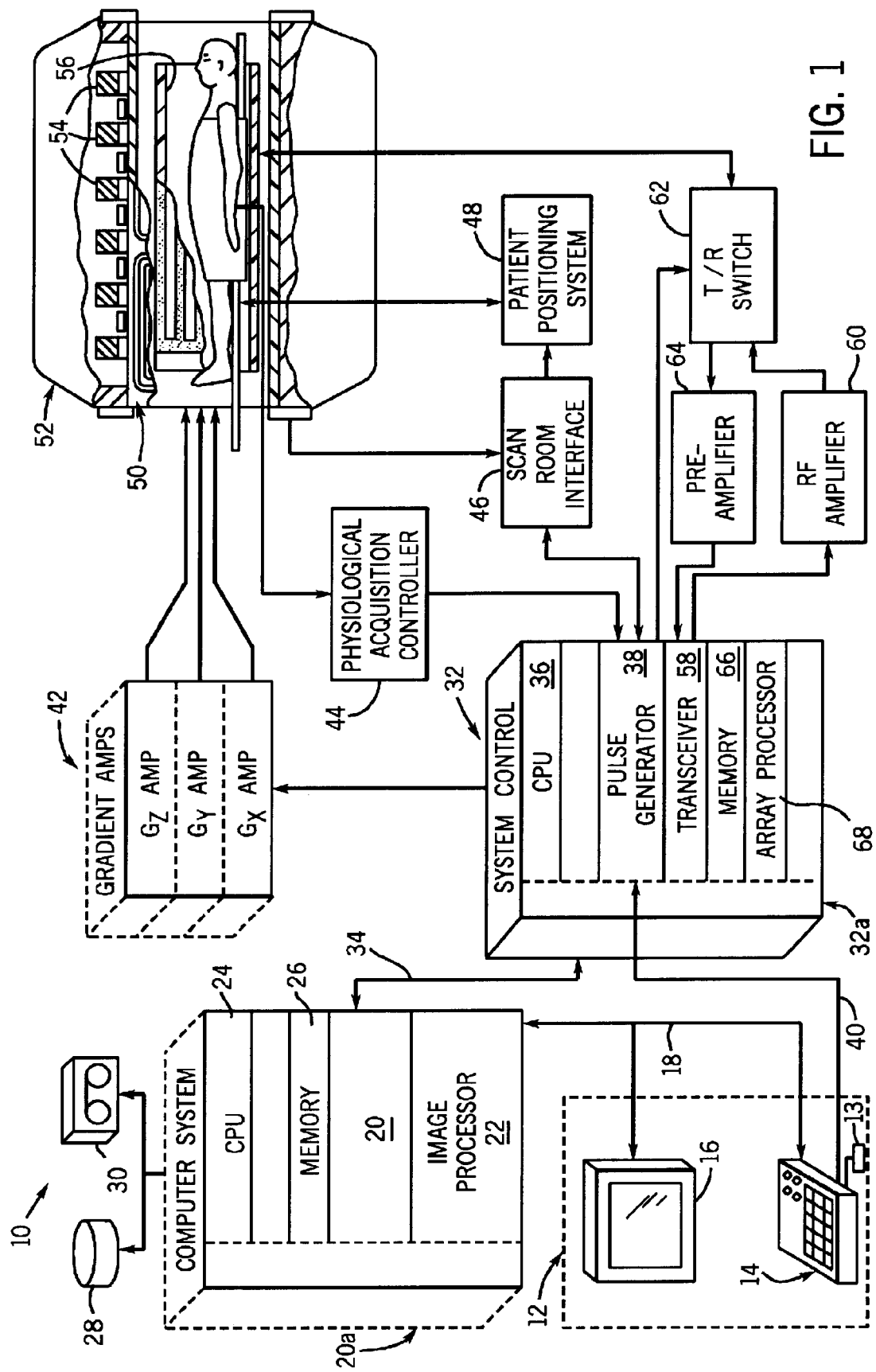
FIG. 1 is a schematic block diagram of an MR imaging system for use with the present invention.

Referring to FIG. 1, the major components of a preferred magnetic resonance imaging (MRI) system 10 incorporating the present invention are shown. The operation of the system is controlled from an operator console 12 which includes a keyboard or other input device 13, a control panel 14, and a display 16. The console 12 communicates through a link 18 with a separate computer system 20 that enables an operator to control the production and display of images on the screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to disk storage 28 and tape drive 30 for storage of image data and programs, and communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicate the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having $G_x$, $G_y$, and $G_z$ amplifiers. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 6Z can also enable a separate RF coil (for example, a surface coil) to be used in either the transmit or receive mode.

The MR signals picked up by the RF coil 56 are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory, such as disk storage 28. In response to commands received from the operator console 12, this image data may be archived in long term storage, such as on the tape drive 30, or it may be further processed by the image processor 22 and conveyed to the operator console 12 and presented on the display 16.

The present invention is directed to a process of obtaining a velocity spectrum of a fluid flowing through a vessel using MR tagging. The invention is particularly directed to a process of acquiring fast measurements of the motion and velocity spectrum of blood flowing through a vessel using MR tagging and acquiring those measurements in a single cardiac cycle. Description of the present invention with respect to the tagging of blood to determine its motion and velocity spectrum is for illustration purposes and is not intended to limit the scope of the invention. That is, the processes embodied in the present invention may be implemented to acquire fast measurements and a velocity spectrum of any fluid flowing through any vessel, including a pipe or other fluid carrying object.

Application of a spatial modulation of a magnetization (SPAMM) tagging pulse sequence in combination with a two-dimensional cylindrical excitation may be used to tag blood flowing through a vessel. The combination of the SPAMM excitation and the 2-D cylindrical excitation enables measuring of velocity spectrum of the blood flowing through the vessel in a single cardiac cycle (heartbeat). Specifically, the cylindrical excitation applied within the vessel lumen encodes signals in a single spatial dimension along the length of the vessel and subsequently collapses MR signals onto an axis along the length of the vessel. One-dimensional projections acquired from the tagged blood provide information about the blood flow through the vessel. The motion and shape of the projections may also be evaluated to gather information regarding the blood flow, such as its velocity spectrum.

Analyzing the projections acquired from the tagged blood reveals that the magnitude of the projections is a function of both space and time, g(z,t), and is affected by several factors including the velocity spectrum of the tagged blood as well as the initial pattern of transverse magnetization following excitation of the blood in the vessel. Additional factors also affect the magnitude of the acquired 1-D projections which must be considered. These additional factors include signal decay, coil sensitivity, and magnetic field inhomogeneity. Preferably, as will be discussed shortly, the impact of these additional factors may be limited by isolating a portion of the vessel in which the impact of those factors is uniform. The impact of the velocity spectrum of the tagged blood may generally be referenced by the following equation:

$$g(z, t) = \left| \int_{-\infty}^{\infty} \tilde{A}(\tau) + M(z - vt) dv \right|; \quad \text{(Eqn. 1)}$$

where $\tilde{A}(v)$ represents the velocity spectrum of the tagged blood and $M(z-vt)$ represents the initial pattern of transverse magnetization following tagging. Additionally, the impact of signal decay, coil sensitivity and magnetic field on homogeneity are collectively represented by a modulation function, $h(v,z,t)$. The acquired projections of the tagged blood may then be considered as a summation of tags of blood moving at different velocities, each of which has the shape of the initial tagging pattern and an amplitude determined by the amount of blood moving at that particular velocity. This summation for each projection may be represented by:

$$g(z, t) = \left| \int_{-\infty}^{\infty} \tilde{A}(v) + M(z - vt) + h(z, v, t) dv \right|; \quad \text{(Eqn. 2)}$$

where g(z,t) represents a matrix of data as a function of position along the axial length of the vessel and time. Acquiring projections over time and stacking each acquired projection as a column of the position-time matrix conveniently displays the evolution of the projections over time. When determining a position-time matrix of projection data using MR tagged blood, it may be possible to ignore the impact of signal decay, coil sensitivity, and magnetic field inhomogeneities when those factors do not greatly affect the projected magnitude of the projection. As a result, the impact of those factors as represented by the modulation function h(v,z,t) may be extracted from the integral shown in Equation 2. The position time matrix using a two-pulse SPAMM excitation to tag the blood may be represented by:

$$g(z, t) = \quad \text{(Eqn. 3)}$$

$$\left| \int_{-\infty}^{\infty} \tilde{A}(v) + \left(1 - \frac{\sin(\alpha)}{2} + (1 - \sin[2\pi k_z(z - vt)])\right) dv \right| + h(z, t);$$

where α is the total SPAMM flip angle and $k_z$ is the spatial frequency of the tags. Moreover and in a specific implementation, if the total SPAMM flip angle, α is 90° the magnitude of the tags follows a sinusoidal pattern. Eqn. 3 is specifically applicable to a sinusoidal tagging pattern, but similar expressions can be derived for other (non-sinusoidal) tagging patterns. As a result, the position-time matrix, g(z,t), simplifies to:

$$g(z,t) \, (\tilde{a}(0) + Im\{e^{Rmax} + \tilde{a}(k,t))\}) + h(z,t); \quad \text{(Eqn. 4)}$$

where $\tilde{a}(k_z t)$ is the Fourier transform of $\tilde{a}(v)$. With a flip angle of 90°, the shape and motion of 1 D projections may be easily calculated for a specific velocity and excitation profile using Eqn. 4. Generally, the velocity profile for laminar flow in a vessel having a radius of R as a function of radial coordinate, r, may be modeled by the general expression:

$$v(\gamma) = v_{\max}\left[1 - \left(\frac{r}{R}\right)^\beta\right] \beta > 1; \quad \text{(Eqn. 5)}$$

where $v_{max}$ is the maximum velocity, and β is a real number. As β approaches infinity, a more plug-like profile results. Additionally, a value of β=2 corresponds to a parabolic laminar flow profile. The velocity spectrum for flow modeled by Eqn. 5 may be defined by the following expression:

$$A(v) = \frac{2}{\beta + v_{\max}}\left(1 - \frac{v}{v_{\max}}\right)^{2\beta - 1} v \in [0, v_{\max}] \quad \text{(Eqn. 6)}$$

While Eqn. 6 describes the velocity spectrum for the entire vessel, the excitation profile determines the region of the velocity profile that contributes to the MR signal. Specifically, the form of $\tilde{A}(v)$ approaches that of the full spectrum $A(v)$ as the flow becomes more plug-like or the excited cylinder encompasses more of the vessel.

For parabolic blood flow and a cylindrical excitation of radius $r_{max}$, the position time matrix may be given by:

$$g(z,t) \, (r_{max}/R)^2 + (1 + \sin c[k_z t \Delta v] + \sin[2\pi k_z (z - \langle v \rangle t)]); \quad \text{(Eqn. 7)}$$

where Δv and <v> are the velocity range and mean velocity of the velocity spectrum of the tagged blood, respectively. Equation 7 represents a sinusoidal projection moving at velocity <v> and temporally modulated by a sinc envelope. As a result, zeroes of the sinc envelope form and are a result of complete destructive interference of the tagging pattern across the vessel, which occurs when the displacement between the fastest and slowest moving blood is an even multiple of the tagging period. For example, if $k2 \cdot v_{max} = 0.05$ msec$^{-1}$ and the entire vessel is excited, the tags will periodically disappear every 20 msec. The frequency of the zeros may be decreased by exciting a more narrow region in the vessel but at a cost of reducing the maximum strength of the signal. Typically, the excitation or tagged region in the vessel is not perfectly sharp and a Gaussian excitation profile with a width of σ results. With a Gaussian excitation profile, and ignoring any projections from static tissue outside the vessel, the velocity spectrum of the excited region in the vessel becomes:

$$\tilde{A}(v) = A(v) + \exp\left[\frac{-R^2}{2\sigma^2}\left(1 - \frac{v}{v_{\max}}\right)^{2\beta}\right]$$ (Eqn. 8)

Further, assuming parabolic flow, the mean velocity of the velocity spectrum of the excited volume as defined by Eqn. 8 is given by the equation:

$$\langle v \rangle = v_{\max} + \left[\left(1 - e^{\frac{-R^2}{2\sigma^2}}\right)^{-1} - 2\sigma^2/R^2\right],$$ (Eqn. 9)

which converges to $v_{max}$ as $R/\sigma$ approaches infinity.

As indicated previously and in accordance with one embodiment of the present invention, using MR tagging of blood flowing through a vessel, it is possible to determine the shape as well as the motion of a 1-D projection for a specific velocity and excitation profile. In a further embodiment of the present invention, the velocity spectrum of the tagged blood flowing through the vessel may be computed by analyzing sections of the position-time matrix heretofore described. As previously stated, velocity spectra are clinically important for the assessment of stenosis and other cardiovascular conditions. Specifically, and in the context of tagged blood motion, the velocity spectra provides an indication of signal contamination from static tissue present in the vessel. Furthermore, contamination decreases the accuracy of the blood-displacement measurements acquired from the tagged blood.

Figure 2:
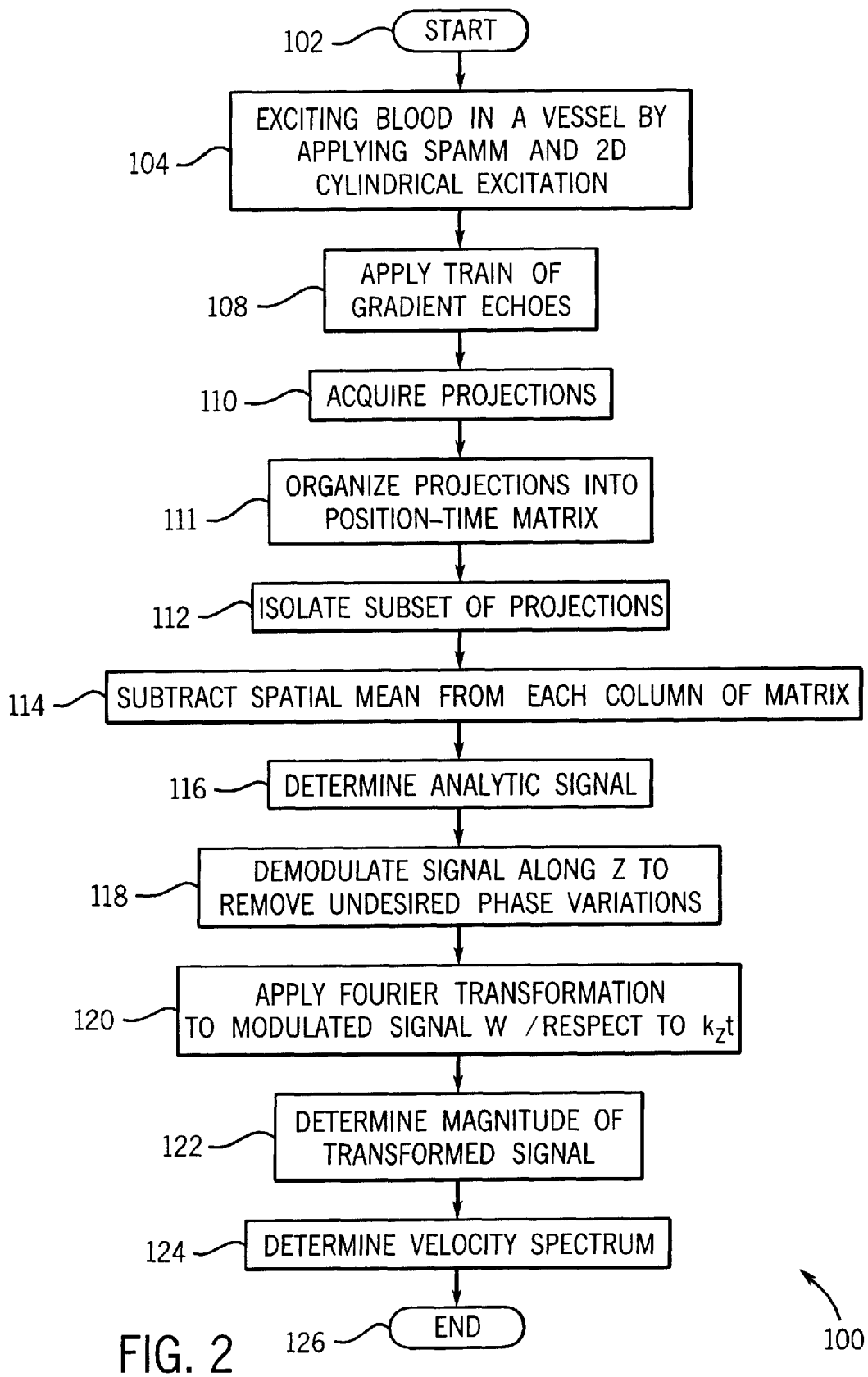
FIG. 2 is a flow chart illustrating the steps of determining a velocity spectrum in accordance with the present invention.

Therefore and in accordance with another embodiment of the present invention, the factors responsible for signal contamination from static tissue are nulled so that more accurate blood displacement may be determined. Referring to FIG. 2, the process 100 for generating a velocity spectrum absent of signal contamination from static tissue begins at 102 with the excitation of blood flowing through a vessel by applying a SPAMM and two-dimensional cylindrical excitation at 104. At 108, a train of gradient echo pulses are applied to the vessel so that a series of 1-D projections of the tagging pattern may be acquired at 110. The series or succession of 1-D projections may then be columnly arranged to form a position-time matrix. The 1-D projections may then be analyzed, as will be discussed, to determine an evolutionary pattern of fluid velocity. That is, the projections may be evaluated to determine a pattern of velocity over time.

Following acquisition of the 1-D projections 110, the projections are organized into a 2-D position-time matrix at 111. Following organization of the projections at 111, a subset of the acquired projections are isolated at 112. The subset of projections is isolated 112 such that the composition of the subset includes those projections in which the velocity spectrum corresponding thereto is steady. While a subset of steady flow projections is isolated, the present invention is not limited to the extraction of a steady flow region of the acquired projections. That is, the present invention may be implemented with different regions of the position-time matrix to construct a velocity spectrum in unsteady flow conditions. At 114, the spatial mean of each projection is subtracted from a corresponding column in the position-time matrix 110. By assuming that the coil sensitivity is uniform across the field-of-view (FOV), and the spatial period of the tags is small relative to the FOV, the spatial mean of each projection may be represented by:

$$\langle g(z,t) \rangle \approx \tilde{a}(0) + h(z,t).$$ (Eqn. 10)

Following subtraction of the spatial mean from each projection at 114, the imaginary operator of the position-time matrix as represented by Eqn. 4 is dropped and an analytic signal is subsequently constructed at 116. In one embodiment, the analytic signal is constructed by applying a Hilbert transform to the spatial dimension of the position-time matrix. Alternatively, however, the Hilbert transform could be applied to the temporal dimension of the matrix, but doing so is less optimal due to signal decay. Further, application of the Hilbert transform is illustrative of only one method that may be used to construct the analytic signal. Other methods may certainly be implemented and are within the scope of this invention.

Following removal of the imaginary operator and construction of the analytic signal at 116, the analytic signal is modulated at 118 using a synchronous homodyne detection technique for removing undesired phase variations from the signal. That is, phase variations introduced by the initial sinusoidal tags are removed by modulating each column of the position-time matrix. That is, phase variations are removed from each acquired projection. As a result, the exponential term from Eqn. 4 is removed. Rather than assuming a specific modulation frequency, the frequency to be used in modulating the signal is measured from the analytic signal of the first projection. That is, the modulating frequency is ascertained from the first projection in the position-time matrix acquired at 110. The frequency of the first projection is selected because, under most circumstances, it is the least affected by signal decay.

The Fourier transformation of the modulated signal is then taken at 120 with respect to the product of spatial frequency and time. That is, the signal decay envelope undergoes a transformation, such as and preferably, a Fourier transformation.

Using the magnitude of the transformed position-time matrix 110, a velocity spectrum is configured at 124. By acquiring a series of projections from the tagged blood, an evolution of the blood flow over time may be determined and shown in accordance with the velocity spectrum 124. Because a SPAMM excitation was used to tag the blood flowing through the vessel and since each projection was independently and individually analyzed, a velocity spectrum of several projections acquired in a single heartbeat or cardiac cycle may be constructed. That is, each 1-D projection provides a measurement of blood motion with high temporal resolution. Therefore, implementation of process 100 in accordance with the present invention does not require that data from multiple cardiac cycles be combined to improve temporal resolution. Ultimately, process 100 provides a velocity spectrum for blood flow through a vessel in a single cardiac cycle by using a succession of acquired projections, each projection having high temporal resolution. After construction of the velocity spectrum at 124, the process ends at 126.

Figure 3:
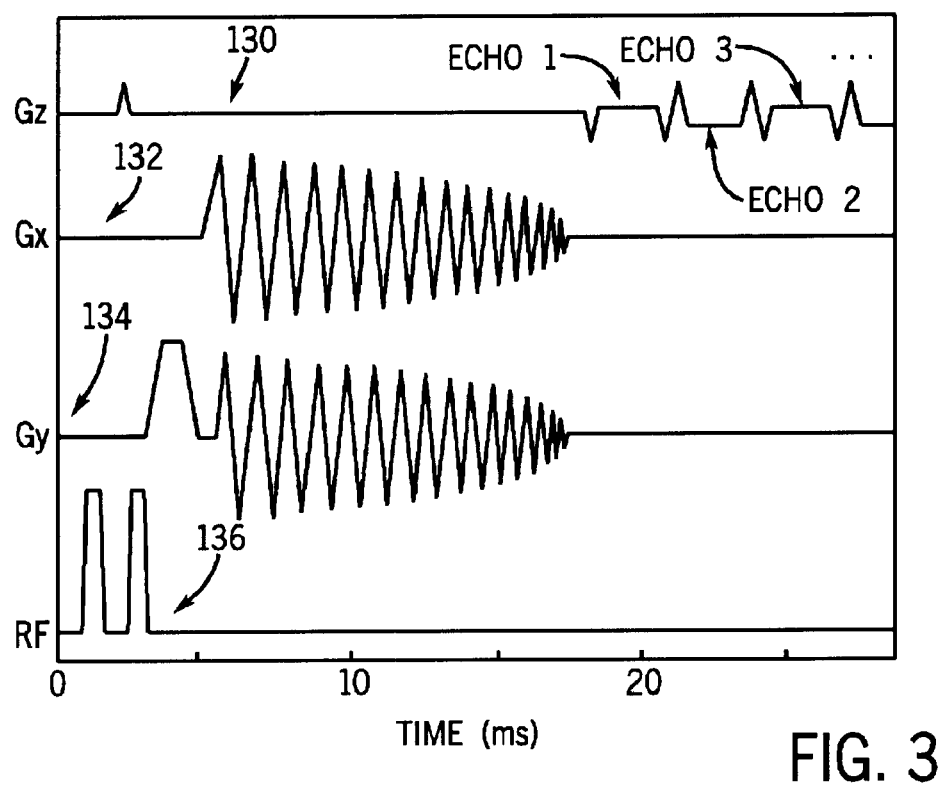
FIG. 3 is a chart illustrating a representative pulse sequence for use in the present invention.

Referring to FIG. 3, a 3D selective excitation and gradient echo-pulse sequence is shown. This exemplary pulse sequence is used to measure velocity spectra as previously set forth. After application of an RF pulse sequence 136, a SPAMM excitation pulse 132 sinusoidally modulates the amplitude of the signal along the vessel of interest. A 2-D cylindrical excitation 134 excites the fluid flowing through and within the vessel. A train of 32–256 gradient echoes 130 is collected using an MR system such as a GE SIGNA® Lx 1.5 Tesla MR system. SIGNA® is a registered trademark of General Electric Company. Further, a chemical saturation pulse (not shown) may be used before the SPAMM excitation signal 134 to reduce signal from fat.

Figure 4:
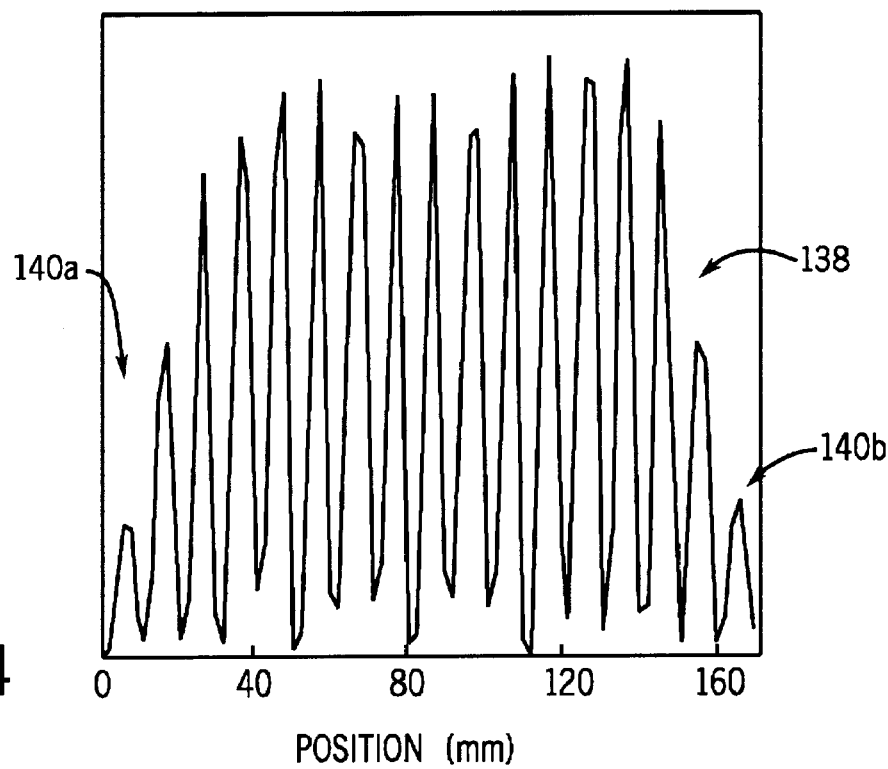
FIG. 4 is a graph representative of a 1-D projection acquired from a phantom in accordance with the present invention.

Now referring to FIG. 4, a representative 1D projection corresponding to the first echo of the readout gradient 130, FIG. 3, measured in a uniform phantom is shown. Projection 138 was experimentally acquired using a 2-D RF pulse comprising a 16 loop gradient spiral lasting 12 msec. A 12 msec pulse duration was selected to allow the excitation of narrow vessels and may be shorter for larger-diameter vessels. The orientation of the vessel used during experimentation was prescribed graphically using a series of spin-echo scout images. The spatial period of the excited fluid or tags varied, but was typically within the range of 5–20 mm. This spatial period was selected to avoid aliasing, which occurs when 1D projections move more than one-half their spatial period between consecutive projections. A train of 32–256 gradient echoes, as illustrated by signal 130 of FIG. 3, was collected after excitation or tagging using a five inch diameter surface coil and a sampling bandwidth of ±32 kHz. The spatial resolution of the projection was chosen to satisfy the requirements of the Nyquist sampling rate of the tagging pattern. 1-D projections were collected every 2–8 msec depending upon the number of samples per echo, which varied between 64 and 256. Projection 138 is representative of a projection acquired during experimentation and having a tagging period of 10 mm. It should be noted that the decrease in amplitude at the edges 140A, 140B of projection 138 was a result of coil sensitivity.

Figure 5:
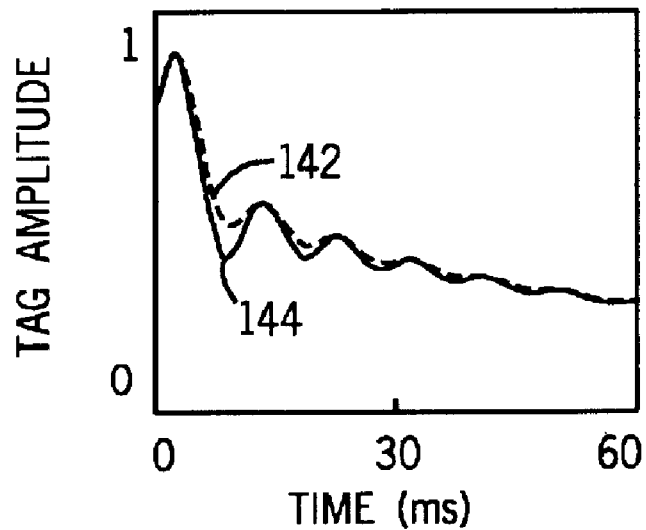
FIG. 5 is a graph illustrating tag amplitude over time for a cylindrical profile and a Gaussian profile in accordance with the present invention.

Now referring to FIG. 5, simulated tagging data for two different flow conditions in accordance with the present invention is shown. Specifically, tag interference of tags flowing at different velocities at one location is shown for a cylindrical profile 142 and a Gaussian profile 144. Each line of simulated data 142, 144 represents one row of a position-time matrix acquired in accordance with the present invention. Further, the simulated data lines 142, 144 include signal decay. As shown, the amplitude of tag interference for both profiles 142, 144 approaches a relative magnitude of one and quickly decays over time.

Figure 6:
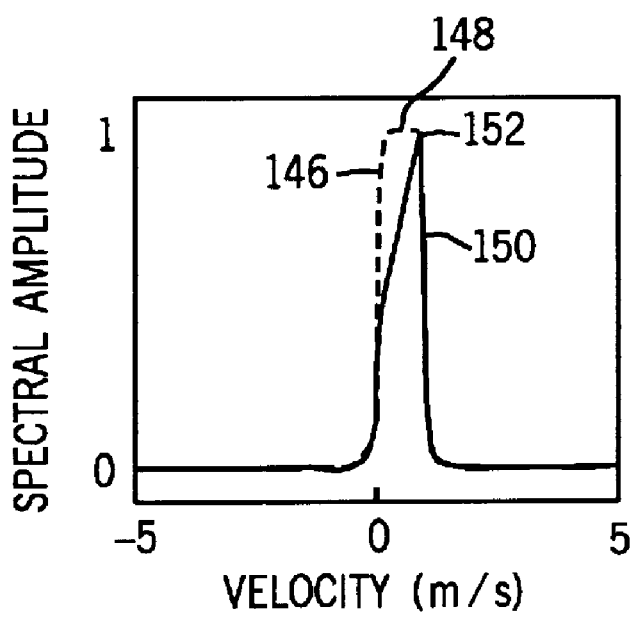
FIG. 6 is a graph illustrating a velocity spectrum of the projections shown in FIG. 5 in accordance with the present invention.

Referring to FIG. 6, representative velocity spectra for each projection corresponding to data lines 142, 144 of FIG. 5 are shown. Specifically, the velocity spectrum for the cylindrical profile 146 reaches its peak 148 more quickly than the Gaussian profile 150. Further, the velocity spectrum for the Gaussian profile 150 maintains its maximum 152 for a shorter period than the cylindrical profile over the same velocity.

Therefore, in accordance with an embodiment of the present invention, a method of measuring of a fluid flow in a vessel comprises the steps of identifying a vessel for fluid flow analysis and applying a pulse sequence to the vessel to excite fluid in the vessel. Application of the pulse sequence to the vessel further produces a sinusoidal variation of transverse magnetization along a column of fluid in the identified vessel. The method further includes the steps of acquiring a set of gradient echoes from the excited fluid in the column of fluid where each gradient echo represents a 1-D projection of the excited fluid across the vessel and tracking an evolution of at least a portion of the 1-D projections. The method also includes the step of developing a velocity spectrum from the evolution tracking.

In a further embodiment of the present invention, a computer program is provided that when executed by the computer causes the computer to apply a SPAMM excitation and cylindrical excitation to fluid flowing through a vessel. The computer is also programmed to acquire a set of gradient echoes from excited portions of fluid flowing through the vessel and determine a 1-D projection from each gradient echo. The computer program further causes the computer to organize the 1-D projections into a matrix where each column of the matrix represents a single 1-D projection and to modulate each column of the matrix to remove phase variations from the 1-D projections. The computer program further causes the computer to determine the magnitude of each 1-D projection and develop an evolutionary map representative of projection over magnitude over time.

In yet a further embodiment of the present invention, an MR apparatus includes an MRI system having a plurality of coils positioned about a bore of a magnet to impress a polarizing magnetic field. The MRI system further includes an RF transceiver system and an RF switch controlled by a pulse module to transmit and receive RF signals to and from a multi-coil RF coil assembly to acquire MR images. The MR apparatus further includes a computer program to apply a tagging sequence to a vessel to excite blood flowing through the vessel to produce a sinusoidal variation of transverse magnetization along a region of blood in the vessel. The computer is further programmed to acquire a series of gradient echoes from the excited blood in the region of blood in a single cardiac cycle and apply a transform to each gradient echo to produce a corresponding 1-D projection. The computer is also programmed to analyze the 1-D projections to determine an evolutionary pattern of blood velocity.

The present invention has been described with particular reference to monitoring blood flow through a vessel. This, however, is only one exemplary representation of the present invention. The present invention is also applicable with measuring/monitoring fluid flow through any fluid carrying configuration.

The present invention has been described in terms of the preferred embodiment, and it is recognized that equivalents, alternatives, and modifications, aside from those expressly stated, are possible and within the scope of the appending claims.

What is claimed is:

1. A method of measuring fluid flow in a vessel comprising the steps of:

identifying a vessel for fluid flow analysis;

applying a pulse sequence to the vessel to excite fluid in the vessel and produce a variation of transverse magnetization along a column of fluid in the identified vessel;

acquiring a set of gradient echoes from the excited fluid where each gradient echo represents a 1-D projection of the excited fluid across the vessel;

tracking an evolution of at least a portion of the 1-D projections; and determining velocity of the fluid flow from the evolution tracking.

2. The method of claim 1 wherein the velocity determining step is further defined as developing a velocity spectrum based on the evolution tracking and then determining the fluid flow velocity from the velocity spectrum.

3. The method of claim 1 further comprising the step of transforming each gradient echo to acquire a 1-D projection of the excited fluid across the vessel.

4. The method of claim 1 wherein the step of applying a pulse sequence includes applying a SPAMM excitation followed by a 2-D cylindrical excitation oriented within the vessel.

5. The method of claim 1 further comprising the steps of:

forming a position-time matrix where each column of the position-time matrix represents a single 1-D projection; and stacking the 1-D projections from a succession of gradient echoes as columns of a 2-D matrix to track the evolution of at least a portion of the 1-D projection.

6. The method of claim 1 further comprising the step of defining a tagging pattern wherein the 1-D projections represent a summation of tags moving at different velocities.

7. The method of claim 6 wherein each tag has a shape of an initial pattern of transverse magnetization and an amplitude that is a function of an amount of fluid moving at a certain velocity.

8. The method of claim 5 wherein the velocity is determined by analyzing sections of the position-time matrix.

9. The method of claim 2 wherein the fluid is blood, the vessel is a blood vessel of a patient, and wherein the set of gradient echoes is collected within a single cardiac cycle.

10. The method of claim 9 further comprising the steps of tagging a column of blood in a blood vessel by combining a 1-D sinusoidal excitation with a 2-D cylindrical excitation and acquiring a series of one-dimension projections.

11. The method of claim 10 wherein the step of developing the velocity spectrum is further defined as analyzing an interference between tags moving at different velocities thereby using magnitude tagging to obtain the velocity spectrum.

12. The method of claim 10 wherein a velocity of a tag equals a mean velocity of the excited blood when the velocity spectrum is symmetric about a velocity spectrum mean velocity.

13. A computer program representing a set of instructions that when executed by a computer causes the computer to:
apply a SPAMM excitation and cylindrical excitation to fluid flowing through a vessel;
acquire a set of gradient echoes from excited portions of fluid flowing through the vessel;
determine a 1-D projection from each gradient echo;
organize the 1-D projections into a number of subsets wherein each subset represents a single 1-D projection;
demodulate each subset of 1-D projections to remove phase variations from the projections;
determine a magnitude of each projection; and
develop an evolutionary map representative of projection magnitude over time.

14. The computer program of claim 13 wherein the computer is further programmed to develop a velocity spectrum of the fluid flowing through the vessel from the evolutionary map of projection magnitude.

15. The computer program of claim 13 wherein the computer is further programmed to subtract a spatial mean of each 1-D projection from a corresponding subset.

16. The computer program of claim 15 wherein the computer is further programmed to construct an analytic signal from the 1-D projections.

17. The computer program of claim 16 wherein the 1-D projections are organized into a position-time matrix computer is further programmed to apply a Hilbert transform to one of a spatial dimension and a temporal dimension of the matrix.

18. The computer program of claim 17 wherein the computer is further programmed to apply synchronous homodyne detection to the matrix.

19. The computer program of claim 14 wherein the velocity spectrum of the fluid is represented by:

$$\tilde{A}(v) = A(v) + \exp\left[\frac{-R^2}{2\sigma^2}\left(1 - \frac{v}{v_{\max}}\right)^{2\beta}\right]$$

where
A (v) represents a velocity spectrum of the vessel;
β represents a real number;
$v_{max}$ represents a maximum velocity of the fluid;
σ represents a width of a Gaussian profile;
v represents an instantaneous velocity of the fluid;
and R represents a radius of the vessel.

20. The computer program of claim 19 wherein the velocity spectrum of the fluid represents a region of a velocity profile that contributes to an MR signal, wherein the velocity profile is represented by:

$$v(\gamma) = v_{\max}\left[1 - \left(\frac{r}{R}\right)^{\beta}\right] \beta > 1;$$

where r represents a radial coordinate.

21. An MRI apparatus comprising:
a magnetic resonance imaging (MR) system having a plurality of coils positioned about a bore of a magnet to impress a polarizing magnetic field and an RF transceiver system and an RF switch controlled by a pulse module to transmit and receive RF signals to and from multi-coil RF coil assembly to acquire MR images; and
a computer programmed to:
apply a tagging sequence to a vessel to excite blood flowing through the vessel and produce a sinusoidal variation of transverse magnetization along a region of blood in the vessel;
acquire a series of gradient echoes from the excited blood in a single cardiac cycle;
apply a transform to each gradient echo to produce a corresponding projection; and
analyze the projections to determine an evolutionary pattern of blood velocity.

22. The MRI apparatus of claim 21 wherein the computer is further programmed to construct a velocity spectrum of the blood flowing through the vessel from the evolutionary pattern of blood velocity.

23. The MR apparatus of claim 21 wherein the tagging sequence includes a SPAMM excitation and a 2-D cylindrical excitation.

24. The MRI apparatus of claim 21 wherein the computer is further programmed to determine a magnitude of interference between excited regions of the blood flowing through the vessel.

25. The MRI apparatus of claim 21 wherein the projections are 1-D projections and are indicative of a summation of excited regions of the blood flowing through the vessel, the excited regions having different flow velocities.

26. The MRI apparatus of claim 25 wherein the summation is represented by:

$$g(z, t) = \left|\int_{-\infty}^{\infty} \tilde{A}(v) + M(z - vt) + h(z, v, t)dv\right|;$$

where
$\tilde{A}$ (v)·M(z–vt) represents an initial pattern of transverse magnetization; and
h(z, v, t) represents a modulation function that accounts for signal decay, coil sensitivity, and magnetic field inhomogeneities.

27. The MRI apparatus of claim 25 wherein the summation is represented by:

$$g(z,t) = \left| \int_{-\infty}^{\infty} \tilde{A}(v) + \left(1 - \frac{\sin(\alpha)}{2} + (1 - \sin[2\pi k_z(z - vt)])\right) dv \right| + h(z,t);$$

where $\tilde{A}(v)$ represents a velocity spectrum within the vessel;

$\alpha$ represents a total flip angle;

$k_z$ represents a spatial frequency of the tags; and $h(z, t)$ represents a modulation function independent of velocity.

28. The MRI apparatus of claim 21 wherein the computer is further programmed to generate an MR signal from blood upon application of the tagging sequence and subsequent displacement of the excited blood produces measurable interference.

* * * * *